(12) United States Patent
Bom et al.

(10) Patent No.: US 6,280,725 B1
(45) Date of Patent: Aug. 28, 2001

(54) COMPOSITIONS AND METHODS FOR INHIBITING THE GROWTH OF FUNGI

(75) Inventors: Isaac Bom, Vlaardingen; Stanley Brul, Vllaardingen, both of (NL)

(73) Assignee: Lipton, division of Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 09/484,748

(22) Filed: Jan. 18, 2000

(51) Int. Cl.$^7$ .......................... A61K 38/43; A01N 25/34; A01N 25/00
(52) U.S. Cl. .......................... 424/94.1; 424/404; 424/405
(58) Field of Search .................................. 424/404, 405, 424/424, 461, 94.1

(56) References Cited

U.S. PATENT DOCUMENTS 5,888,504    3/1999  Brul et al. .

FOREIGN PATENT DOCUMENTS

| 0 867 125 A1 | 9/1996 | (EP) . |
|---|---|---|
| 63185358 | 5/1988 | (JP) . |
| WO 93/04588 | 3/1993 | (WO) . |
| WO 96/28468 | 9/1996 | (WO) . |
| WO 97/01348 | 1/1997 | (WO) . |
| WO 97/14310 | 4/1997 | (WO) . |
| WO97/16973 | 5/1997 | (WO) . |

OTHER PUBLICATIONS

Granot et al. Carbon Source Induces Growth of Stationary Phase Yeast Cells, Independent of Carbon Source Metabolism; Yeast, vol. 9, pp. 465–479, 1993.*

Kurasawa et al. *Appl. Environ. Microbiol.*, 58(*1*), 106–110 (1992), in *Chem Abst, 116*, 102396.

* cited by examiner

Primary Examiner—Jon P. Weber
Assistant Examiner—Patricia D Patten
(74) Attorney, Agent, or Firm—James J. Farrell

(57) ABSTRACT

A composition suitable for inhibiting the outgrowth of fungi is provided comprising a first ingredient which inhibits the biogenesis of a normal fungal cell wall and a second ingredient which is capable of perturbing the structure of the cellular membrane of said fungi, so that either the cellular integrity is essentially lost or cell division cannot take place, or both. The first ingredient preferably inhibits the anchorage of cell wall proteins in the cell wall of the fungi and is suitably a β-(1,6)-glucose polysaccharide, preferably β-gentiobiose or a pustulan fragment. The second ingredient is suitably a natural microbial membrane affecting substance (MMAS), preferably MB-21. The composition is particularly suitable as a preservative for inhibiting the outgrowth of fungi in food products, such as sauces, dressings, ketchups, and soups, but is also useful for preventing or inhibiting undesired fungal growth on other products such as personal health care products, e.g. soap bars.

8 Claims, 8 Drawing Sheets

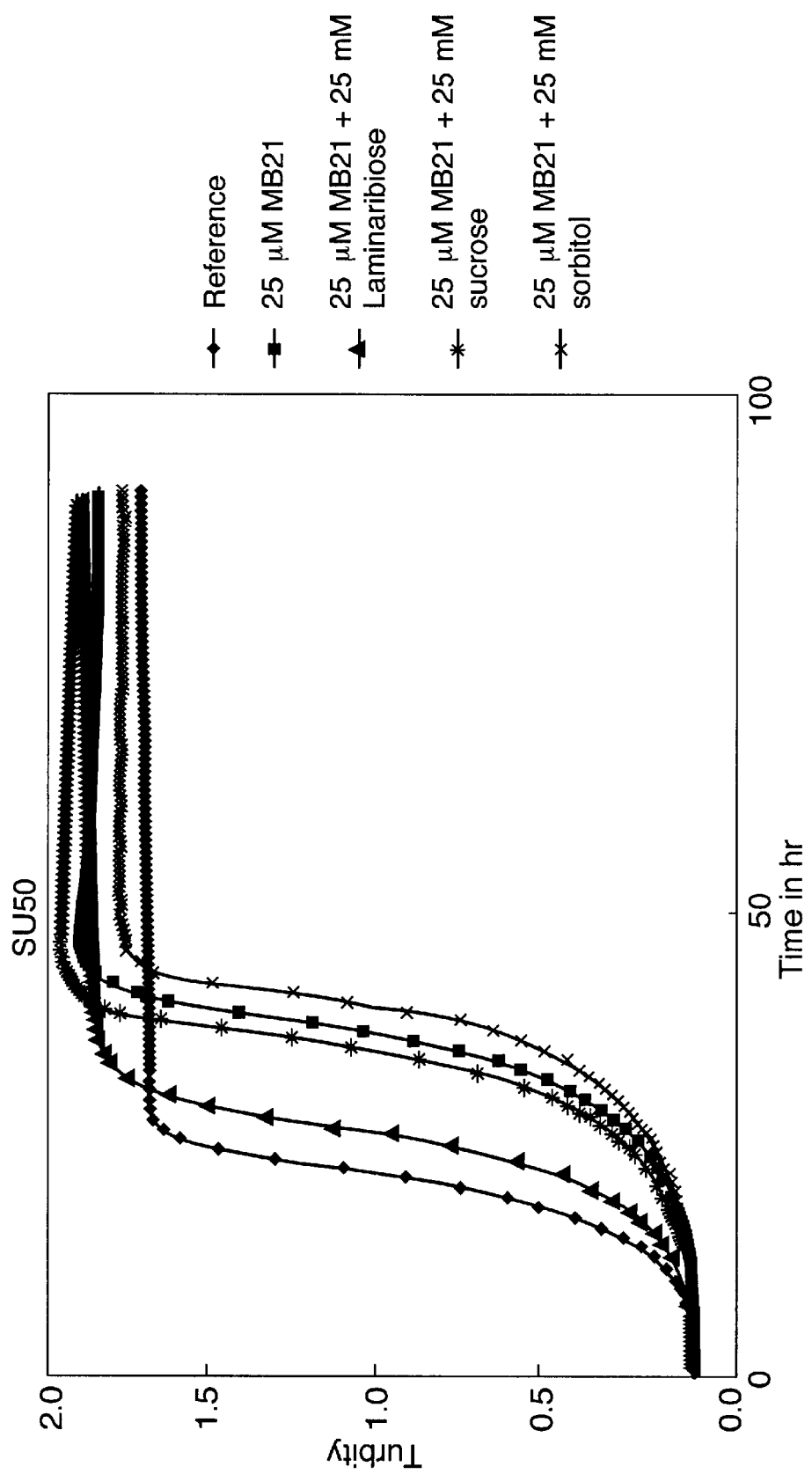

ZB

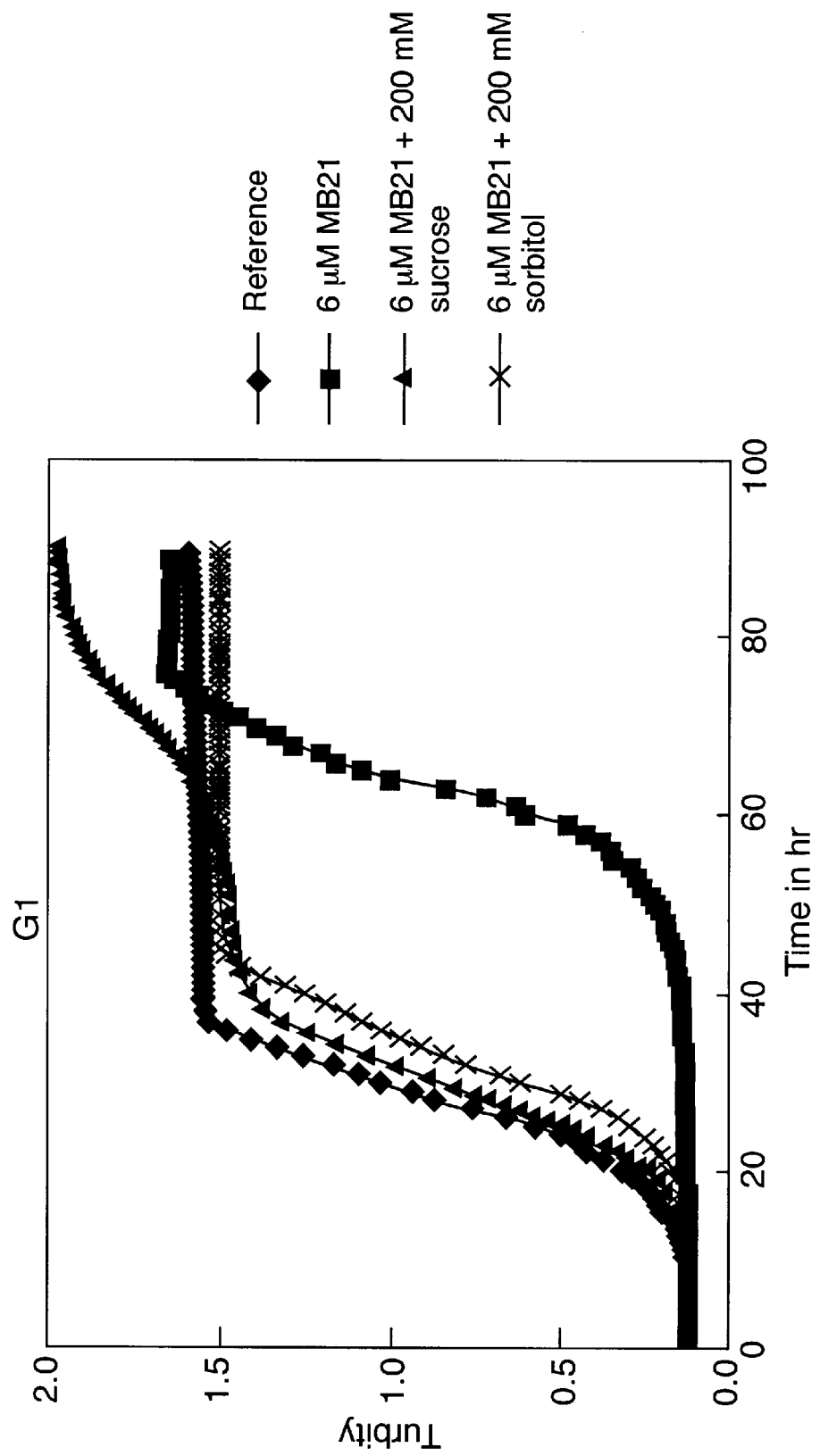

COMPOSITIONS AND METHODS FOR INHIBITING THE GROWTH OF FUNGI

FIELD OF THE INVENTION

The present invention relates to antifungal compositions and to methods for applying such compositions, in particular in the preservation of food against deterioration by fungal growth.

BACKGROUND OF THE INVENTION AND STATE OF THE ART

It is known that a variety of compounds have fungistatic properties and can therefore be used to inhibit the growth of fungi in a product. However, many fungistatic compounds are generally not accepted in food products or they have a non-natural image.

WO 97/16973 (Unilever) discloses compositions suitable for combating fungi in food and other products such as personal care products, comprising the combination of a fungal cell wall lytic enzyme and a natural microbial membrane affecting substance (MMAS), in an effective concentration. The preferred enzymes are chitinase, β-(1,3)-glucanase and β-(1,6)-glucanase. The MMAS is exemplified by nisin, amphiphilic alpha-helix forming peptides, such as histatins and the polypeptide FASLLGKALKALAFQ (=Phe-Ala-Ser-Leu-Leu-Gly-Lys-Ala-Leu-Lys-Ala-Leu-Ala-Lys-Gln) (SEQ ID No:1), and fungal inhibitors, such as carvacrol and sorbic acid. MMAS are present in herbs suitable for food preparation and also herbs suitable for cheese manufacture, especially chives, curcuma and garlic.

However, further research has shown that the fungistatic compounds described in WO 97/16973 are not always heat stable so that they become partly or completely inactivated when the products incorporating them are heated to achieve pasteurisation or even sterilisation.

WO 97/14310 describes the combination of saccharides in general with biocidal active component for combating plant pathogens.

EP 867125 describes combinations of water-soluble hemicellulose in general with a component from a range of preservatives, for preserving food and drinks.

WO 93/04588 discloses combinations of chelating agents and lanthionines (amongst which is nisin) as antimicrobial compositions. Among the chelating agents are mentioned polyols, saccharides, polyethylene glycol.

JP 63/185358 describes combinations of starch hydrolysates with one of glycine, maltose, ethanol, sorbic acid, lysozyme, edible salts of acetic acid for preservation.

Chemical Abstracts 116 (11), Mar. 16, 1992 (Kurusawa et al) describe the induction of cellulase by β-gentiobiose.

Thus, in spite of the success of the approach described above, there is still a need for fungistatic compounds that are sufficiently heat-stable in addition to being acceptable in food products and other products that come in contact with humans, such as personal care products.

SUMMARY OF THE INVENTION

In accordance with the present invention there is provided a composition suitable for inhibiting the outgrowth of fungi characterised in that it comprises a first ingredient which inhibits the biogenesis of a normal fungal cell wall and a second ingredient which is capable of perturbing the structure of the cellular membrane of said fungi, so that either the cellular integrity is essentially lost or cell division cannot take place, or both.

In one aspect of the invention, the first ingredient inhibits the anchorage of cell wall proteins into the cell wall of the fungi. This first ingredient is preferably selected from the group consisting of β-(1,6)-glucose polysaccharides, branched polysaccharides having a β-(1,6)-glucose-backbone, and mixtures thereof. Preferred compounds include β-gentiobiose and pustulan fragments.

In another aspect of the present invention, the second ingredient is preferably selected from the group consisting of natural microbial membrane affecting substance (MMAS). Preferred compounds are nisin, amphiphilic alpha-helix forming peptides such as MB-21, and fungal inhibitors present in herbs suitable for food preparation, such as carvacrol and sorbic acid.

In a further embodiment of the present invention, the first ingredient is preferably present in a concentration of 0.05 to 20 wt. %, more preferably 0.1 to 1 wt. %, calculated on the composition. The second ingredient is preferably present in a concentration of $5\times10^{-5}$ to $1\times10^{-2}$ wt. %, more preferably $1\times10^{-4}$ to $2.5\times1/^{-3}$ wt. %, calculated on the composition.

The compositions of the present invention are suitably used in food products, such as sauces, sauce-bases, dressings, ketchups, soups, soup-bases, spreads, beverages (e.g. tea-based beverages), ice cream, and in personal care products such as skin creams, lotions, ointments, as well as shampoos and other products for application to hair.

These and other aspects will be set out in more detail in the following description and claims.

BRIEF DESCRIPTION OF THE DRAWINGS

FIG. 5a shows the influence of various sugars on the growth of *Saccharomyces cerevisiae.*

FIG. 5c shows the influence of various sugars on the growth of *Zygosaccharomyces bailli* G1.

DETAILED DESCRIPTION OF THE INVENTION

Figure 1:
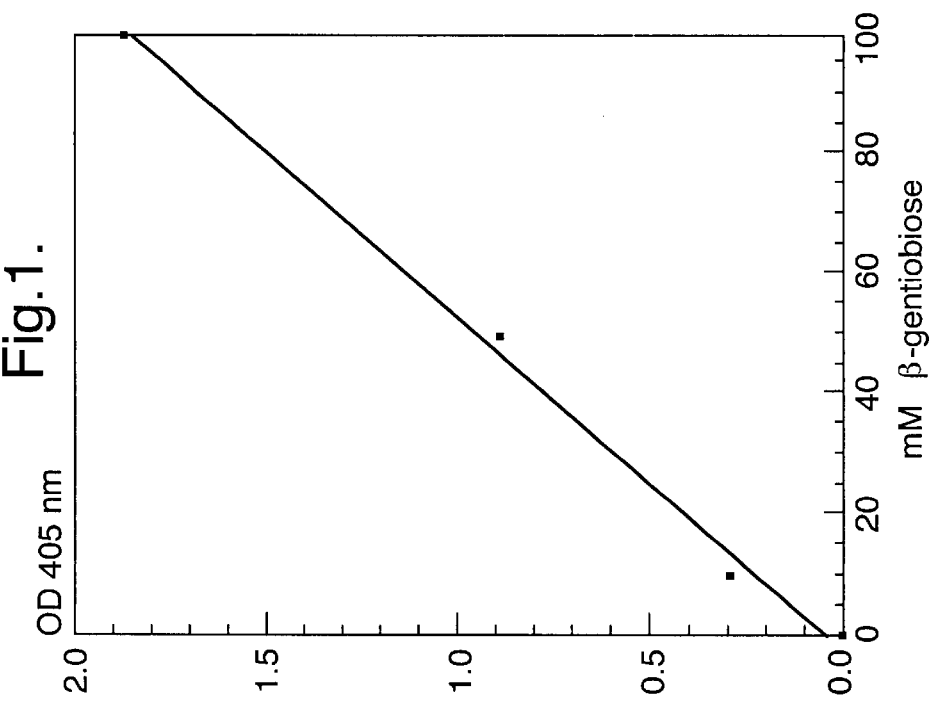
FIG. 1 shows the interrelationship, in a culture medium, between the concentration of β-gentiobiose and the release of the fusion protein α-galactosidase-CW2p from the cell wall.

As used herein, the term "fungi" include moulds and yeasts. Thus, compounds having fungistatic properties are active against moulds or yeasts, or both.

Cell walls are essential for the survival of yeast and fungal cells. The wall protects the cell against mechanical stress, it gives the cell integrity and shape. Moreover, the wall is also a protector against influences from the outside. Important components of the cell wall are polysaccharides and glycoproteins.

In general the cell wall of fungi consist of polymers of β-(1,3)- and β-(1,6)-glucose. Chromatographic analysis of the β-(1,3)-glucan shows a heterogeneous distribution with sizes between approximately 10 and 100 kDa[1]. By comparison, the β-(1,6)-glucose polymer seems to consist of an average of 140 glucose units[1]). In addition to the basic structural glucan components, the mannoproteins are also an important part of the cell wall. Besides these major cell wall components, the wall also consists of chitin, chitosan, polyglucuronic acid, and in Oomycetes of some cellulose. The glucan components have a structural function, whereas the mannoproteins have an important role in controlling the porosity of the cell wall and the susceptibility of fungi to anti-fungal agents[2]). Although β-(1,3)-glucan forms the major part of the cell wall, also β-(1,6)-glucan is very important. β-(1,6)-glucan is ubiquitous in fungi and is responsible for the rigidity of the cell wall, it is the central molecule that keeps structural components together, including β-(1,3)-glucan, mannoproteins and part of the chitin.

There is evidence that chitin and β-(1,3)-glucan are synthesised at the plasma membrane with simultaneous secretion into the periplasmic region The mannoproteins are synthesised at the endoplasmatic reticulum (ER) and modified during the transport through the secretory pathway[5]). Finally, the pathway(s) for the synthesis of β-(1,6)-glucan is still obscure. However, at least a part of the β-(1,6)-glucan synthesis may occur in the ER or Golgi[6]). It is likely that all these components will meet together in the periplasmic region, this is the place where the linkage reactions must take place. Since there is no evidence that high energetic compounds are present at this location, it is likely that reactions leading to cross-linkages are trans-glycosidation reactions. Nowadays, it is generally accepted that the non-reducing end of a β-(1,6)-glucan chain is connected to the GPI remnant of the mannoproteins, and the reducing end to the β-(1,3)-polysaccharides of the cell wall[1]).

The present invention is based on the surprising finding, after intensive research and experimentation, that β-(1,6) glucose polysaccharides dissolved in the medium can enhance the effect of antimicrobial agents, as a result of competition of exogenous and endogenous β-(1,6)-glucan.

Therefore, according to one aspect of the invention, the outgrowth of fungus infection in a product is significantly inhibited by incorporating in such a product, as a first ingredient, at least one β-(1,6)-glucose polysaccharide compound which is able to reduce the content of cell wall proteins on the surface of fungi and, as a second ingredient, one or more fungicidal compounds which are normally used in food products.

Preferred β-(1,6)-glucose polysaccharide compounds contain between 2 and 10 glucose residues, optionally with side-chain glycosylation. Suitable and preferred compounds are the disaccharide β-gentiobiose, and fragmented pustulan preferably having an average molecular weight of $600 \leq x \leq 1000$ Dalton. The second ingredient is suitably selected from the group consisting of natural microbial membrane affecting substances (MMAS). This group includes, for example, nisin, amphiphilic alpha-helix forming peptides such as histatins, dermaseptin, the polypeptide FASLLGKALKALAFQ (SEQ ID NO:1, and fungal inhibitors, such as carvacrol and sorbic acid, which are present in herbs suitable for food preparation. A preferred compound is the antimicrobial peptide MB-21, which is disclosed in WO 96/28468. Preferred and effective combinations comprise β-gentiobiose and/or fragmented pustulan as the first ingredient and MB-21 as the second ingredient.

The first ingredient is effectively present in a concentration of about 0.05 to about 20 wt. %, preferably 0.1 to 1 wt. % calculated on the composition. The second ingredient is effectively present in a concentration of about $5 \times 10^{-5}$ to about $1 \times 10^{-2}$ wt. %, preferably $1 \times 10^{-4}$ to $2.5 \times 10^{-3}$ wt. % calculated on the composition. Concentrations and ratios may be easily optimized by a skilled person depending on the actual composition ingredients. Anti-fungal compositions which are meant to be incorporated in products, contain the active ingredients in an increased concentration taking into account the dilution resulting from mixing.

The term "natural" as used herein refers to the origin of the substance. It means that the substance can be obtained from a natural source, even when the MMAS could also be obtained by synthetic preparation. Therefore the growth of fungi inhibiting composition of the present invention comprises MMAS irrespective of its way of preparation.

The MMAS components useful in the compositions of the present invention are selected, obtained and applied in essentially the same way as described in WO 97/16973, which is incorporated herein by reference.

The new compositions according to the present invention are highly heat stable. Moreover, by the presence of the β-(1,6)-glucose polysaccharide a lower amount of the fungicidal component may be used to achieve at least the same effect as is known from the prior art for compositions with the same fungicide in single form or in another combination. Not only are the costs for preservation lowered in this way because less preservative substance is needed, but even more important form a nutritional point of view is the reduction of the content of non-natural food additives. The preservation ingredients according to the invention are considered to be natural.

The invention further provides compositions which are used as preservation additives and comprise both one or more β-(1,6)-glucose polysaccharides and one or more MMAS components, as well as finished consumer products in which these ingredients are incorporated in effective amounts. For protection against airborne fungi the invention can take the form of dissolving the polysaccharide(s) and MMAS in an aqueous liquid and spraying the solution on the surface of a product which may be a food composition, a cosmetic composition or any other composition which can be affected by fungal growth.

Food products which are suitably treated by the compositions of the present invention include, but are not limited to, w/o-emulsions, spreads, o/w-emulsions, sauces, soups, dressings, mayonnaises, tomato-based products, condiments, fermented products such as soy-sauce, etc. As used herein, the term "food product" also comprises semi-finished products, such as sauce or soup bases which have to be diluted e.g. with an aqueous liquid prior to use.

In another aspect, the invention further relates to the use of the combination of a first ingredient which inhibits the biogenesis of a normal fungal cell wall and a second ingredient which is capable of perturbing the structure of the cellular membrane of said fungi, so that either the cellular integrity is essentially lost or cell division cannot take place, or both, as further specified herein, in the manufacture of a medicament. Preferably, said use is for the manufacture of a medicament for treating fungal infections by topical application.

Beside the active ingredients the composition of the invention may contain auxiliary ingredients which are usual for fungi inhibiting compositions and which include solid diluents, solvents, stabilizers and pH-regulators. The composition may be in the form of a powder, a paste or a liquid, depending on the envisaged way of application.

Although the compositions according to the present invention are particularly suitable as preservatives for inhibiting the growth of fungi in food, they can also be used as well for preventing or inhibiting undesired fungal growth on other products, such as cosmetic products. Examples of cosmetic products include toiletries, e.g. soap bars and shampoos. The cosmetic product may contain the fungi inhibitor not only for remaining itself fungi-free but also for the advantageous effect on the skin which is treated with such product, e.g. a shampoo being applied to a scalp with a fungal affliction.

In the experimental section some typical examples show that by incubating fungal cells in the presence of heat-stable $\beta$-(1,6)-glucan oligomers (i.e. up to 10 glucose units), the cells secrete a substantial amount of their covalently bound protective cell wall mannoprotein layer. These cell wall proteins normally prevent access of MMAS molecules to the plasma membrane. Upon coincubation of fungal cells with a $\beta$-(1,6)-glucan polymer and a MMAS compound (e.g. MB-21), a synergistic growth effect was noted. Both agents are highly heat-stable.

The invention is further illustrated by the following experimental work which is not to be construed as limiting the scope of the invention in any way.

Materials and Methods

Endo $\beta$-(1,6)-glucanase was obtained essentially as decribed in references 9 and 10. Enzyme solutions were prepared and purified in accordance with the same references, inter alia using hydrophobic interaction chromatography.

Pustulan (*Umbilicaria papullosa*) was purchased from Calbiochem and purified by dissolving crude pustulan in hot mili-Q water. After cooling, the solution was micro-filtered. The micro-filtered pustulan was applied to DEAE Sepharose column, running only with mili-Q water. The unbound fraction consisting of pure pustulan was lyophilized.

Pustulan fragments were typically prepared and purified in the following way. To 1 gram purified pustulan, dissolved in 20 ml 50 mM potassium acetate, 75 units $\beta$-(1,6)-glucanase were added. After incubation at 37° C. overnight, the reaction was terminated by heating the mixture at 100° C. for 10 minutes. After cooling to room temperature the solution was micro-filtrated (0.22 $\mu$M) to remove any possible turbidity. The avarage molecular weight of the pustulan fragments was calculated from the increase of reducing sugar, using the 3,5-Dinitrosalicylic acid (DNS) reagent and unfragmented pustulan (Mw 20.000) as a standard. The preparation was shown to contain as major component trimers and tetramers of beta-(1,6)-glucan and was used in the experiments discussed in example 4.

In a different set of tests described in example 2, we used pustulan fragments generated as described above but now of a different size in the range of 800 to >4000 Dalton. The size of the enzymatically fragmented pustulan was steered by adjusting the incubation time with beta-(1,6)-glucanase to 1,5 hours. Subsequently, the mixture was separated on a Biogel P-4 gel filtration column (5×95 cm) previously equilibrated with mili-Q water. Elution was performed with mili-Q water at a flow rate of 20 ml per hour, and fractions of 10 ml were collected. During the gel filtration chromatography, the $\beta$-(1,6)-glucan fragments were analyzed by measuring the refraction index. Fractions were pooled into three portions of 216 ml and one of 144 ml, named fraction one, two, three and four, respectively, after which these fractions were lyophilised. The size of the fragment pools was estimated from their elution pattern on the Biogel P-4 column using molecular size markers.

For examples 2, and 4–9 grow-curves were recorded at 25° C. using a microbiology growth reader (Bioscreen C, ex Labsystems). For example 3, growth curve was determined as turbidity, measured by hand at a wave length of 660 nm (OD 660).

$\beta$-gentiobiose (6-O-$\beta$-glucopyranosyl-$\beta$-D-glucose) was purchased from Sigma Chemical Company.

Centriprepe®, centrifugal concentrators were obtained from Amicon.

All other chemicals were of analytical grade and were purchased from commercial sources.

Organisms, Media and Maintenance

1. Strains
   a) *Saccharomyces cerevisiae* wild type strain SU-50[3,11].
   b) *Saccharomyces cerevisiae* #SU52-pUR5801, containing the $\alpha$-galactosidase-CWP2p construct[3].
   c) *Zygosaccharomyces bailii* ZB (NCYC 563)
   d) *Zygosaccharomyces bailii* G1 (internal strain, isolated from spread)
2. Maintenance of Yeasts Strains
   a) *Saccharomyces cerevisiae* strain SU-50 was cultivated in YEPD medium, supplemented with 2% glucose.
   b) *Saccharomyces cerevisiae* strain SU52-pUR5801 was cultivated in Difco yeast nitrogen base (YNB), supplemented with 2% glucose and 0.004% histidine. After the culture had reached the late log-phase, the cells were cultivated further (a 10% inoculum) in YEPD medium, consisting of 1% Difco yeast extract, 2% Bacto-peptone, supplemented with 0.5% glucose and 5% galactose.
   c) *Zygosaccharomyces bailii* ZB: as SU-50 above.
   d) *Zygosaccharomyces bailii* G1: as SU-50 above.
3. Cell Wall Protein Release Tests and Growth Inhibition
   a) *Saccharomyces cerevisiae* strain SU52-pUR 5801 was grown in YNB and YEPD media, at 30° C. with shaking at 225 rpm in an orbital incubator until a OD (660 nm) between 5 and 6 was reached. In parallel experiments several concentrations of $\beta$-gentiobiose or pustulan fragments were included in the media. After cultivation, the media were separated from the cells by centrifugation (10.000×g for 15 min at 4° C.). The media were then filtered using 0.22 $\mu$M filters. Secretion of $\alpha$-(-galactosidase-CWP2p was assessed by measuring $\alpha$-(-galactosidase enzyme activity in the media (see further on).
   b) Growth curves were obtained with the strain SU-50. The cells (about 10 per ml) were cultured in YEPD at 25° C. in the presence or absence of $\beta$-gentiobiose or pustulan fragments and MB-21, by using a 24 well plate at room temperature with continuous shaking on a micro-titre plate shaker (mark 4) or a microbiology growth reader (Bioscreen C).

Analytical Methods

Preparation of DNS reagent

The 3,5-Dinitrosalicylic acid (DNS) reagent is prepared in the following way. 20 gram 3,5-dinitrosalicylic acid (Merck) is suspended in 400 ml water. While continuously stirring 300 ml sodium hydroxide solution is added (32 g/300 ml water) and the volume is subsequently adjusted to 1.5 L by the addition of water. Stirring is continued until a clear solution is obtained. Next 600 gram Rochelle salt (sodium potassium tartrate, Merck) is added and stirring (and, if necessary, heating) is continued until dissolution. The volume is adjusted to 2 L and the solution filtered, if necessary. The solution is kept at room temperature in the dark and protected against carbon dioxide absorption. The reagent is stable for at least one month.

Determination of the Amounts of Reducing Groups

After enzymatic pustulan hydrolysis was stopped, 1 ml DNS was added. The amounts of reducing sugar groups were determined by heating the test tubes in boiling water for 10minutes, cooling to room temperature, and recording the extinction at 540 nm.

The average molecular weight of the pustulan fragments was calculated from the increase of reducing sugar, using unfragmented pustulan (MW 20.000) as a standard.

α-Galactosidase Assay

α-Galactosidase activity was determined at 37° C. using p-nitrophenyl α-(-D-galactopyranoside (PNPG) as substrate in 0.1 M potassium acetate buffer, pH 5.0. Except where indicated otherwise, the following procedure was employed. A solution of 22.22 mM PNPG in acetate buffer was freshly prepared. 0.1 ml of an enzyme solution diluted in acetate buffer was added to 0.9 ml pre-warmed substrate solution. The mixture was incubated in a thermostatically controlled water bath at 37° C. (±0.1°C.) for 5–10 minutes. The reaction was stopped by addition of 2 ml 10% sodium carbonate solution. A blank was made as described above, adding 0.1 ml potassium acetate buffer to the prewarmed substrate solution. The extinction of the liberated p-nitrophenolate was recorded at 405 nm.

Results

EXAMPLE 1

Competition with β-gentiobiose

β-Gentiobiose was dissolved in YEPD media supplemented with 5% galactose, in concentrations of 10, 50 and 100 mM respectively. After cultivating the strain SU52-pUR5801 in YNB, the cells were cultivated further in the β-gentiobiose galactose containing YEPD media at 30° C., with shaking at 225 rpm in an orbital incubator for 18 hours. The media were separated from the cells by centrifugation (10,000 g for 15 min at 4° C.); subsequently the media were filtered using 0.22 μM filters. To reduce the relative high concentration of galactose in the medium, buffer exchange was performed using PD-10 gelfiltration, previously equilibrated with 50-mM potassium acetate buffer pH 5.0. The enzyme activity of the fusion protein CWP2-α-galactosidase was measured as described in the α-galactosidase assay. The relationship between the β-gentiobiose concentration and the release of the fusion protein α-(galactosidase-CW2p from the cell wall is shown in FIG. 1. It appears that the secretion of the fusion construct is concentration dependent. A linear relationship was found between concentration and secretion, at least up to 100 mM β-gentiobiose.

EXAMPLE 2

Competition with Pustulan Fragments

Figure 2:
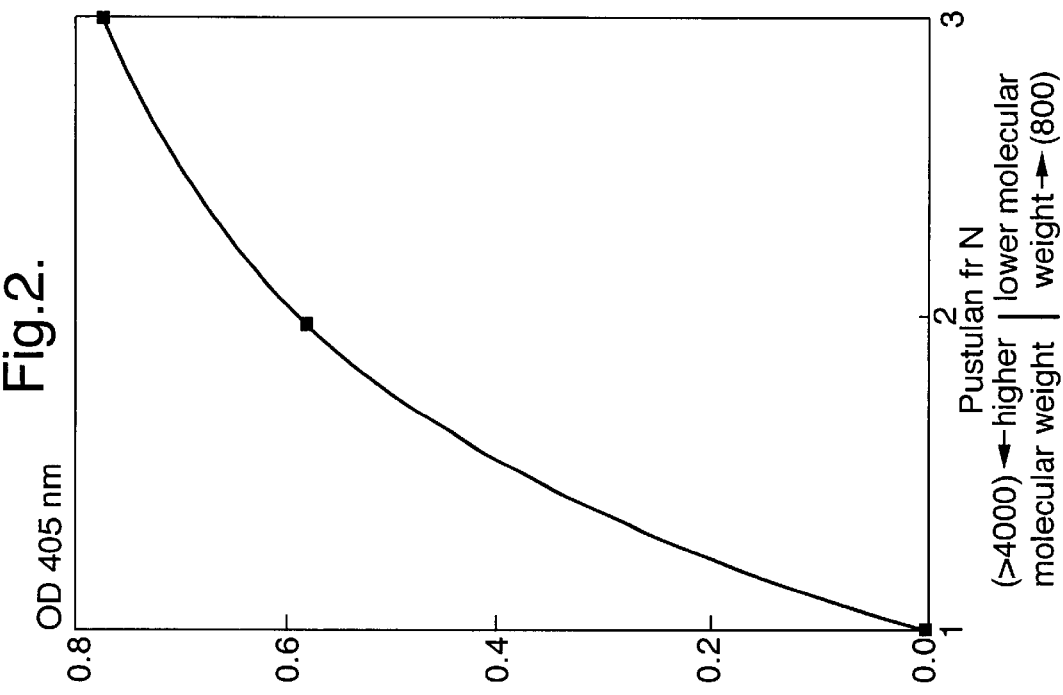
FIG. 2 shows the effect of fragmented pustulan (i.e. various sizes of β-(1,6)-glucan fragments) on the release of α-(-galactosidase-CW2p from the cell wall, measured in a culture medium.

Similarly, this example shows the competition between the secretion of a typical cell wall protein and its incorporation in the cell wall under the influence of pustulan fragments. Several YEPD media were prepared. The media contain MB21 and MB21 plus pustulan fragments in concentrations of 20 μM and 2 mM, respectively (pH 6.5). Saccharomyses cerevisiae SU-50 was inoculated in YEPD as such, and in the supplemented media in a concentration of 50 cells per ml. Samples (200 μl) were pipetted into a Honeywell plate and grow-curves were recorded at 25° C. using a microbiology growth reader (Bioscreen C). FIG. 2 shows the effects of the additions of growth.

EXAMPLE 3

Growth Inhibition with Various Concentrations of β-gentiobiose and/or MB21

Figure 3:
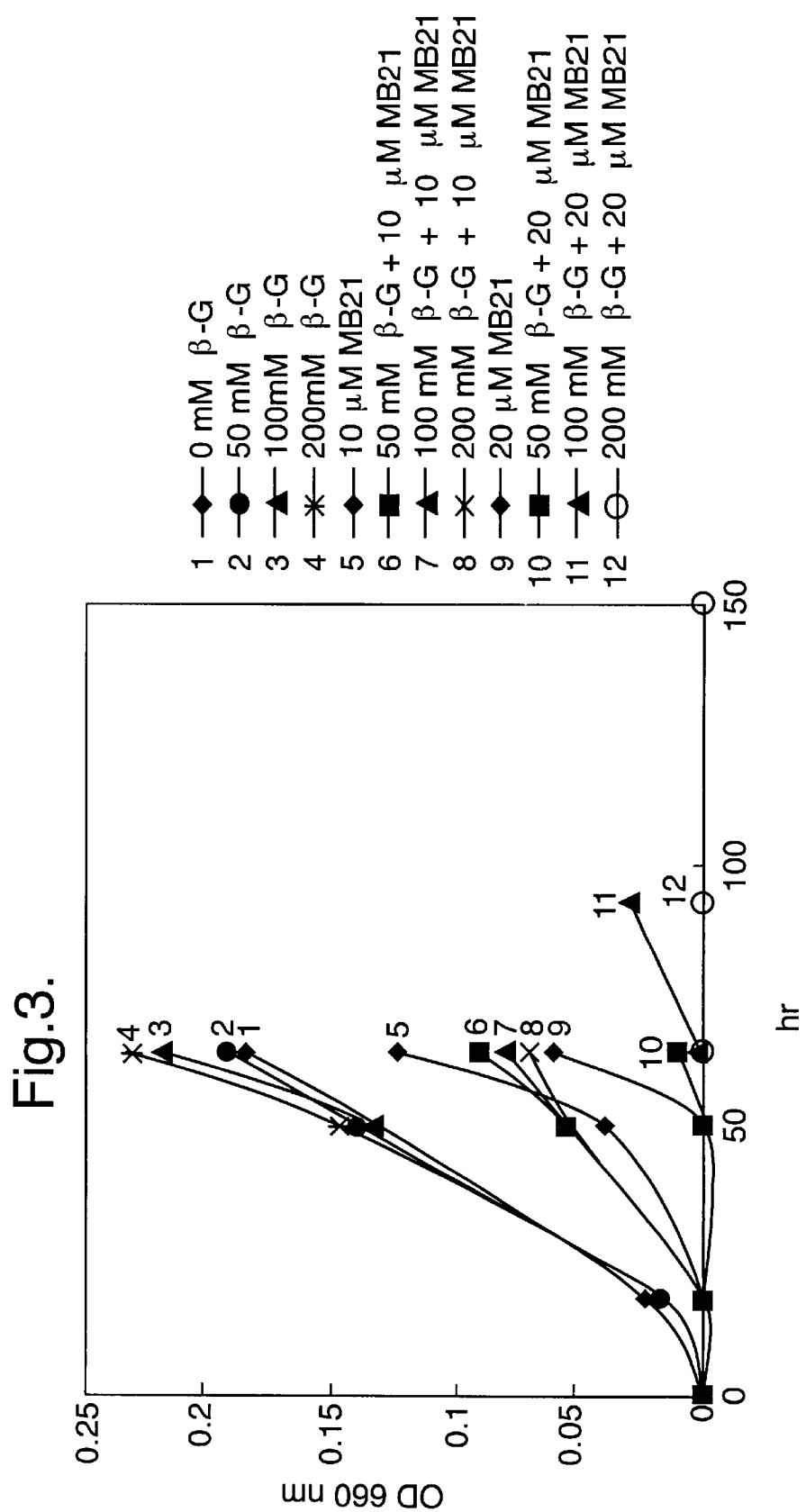
FIG. 3 is a set of graphs showing the effect of combinations of β-gentiobiose and MB-21 at various concentrations on the growth of a wild type yeast.

Three YEPD media were prepared, one without MB21, the other YEPD media contained 10 μM MB21 and 20 μM MB21, respectively. To these media β-gentiobiose was added in concentrations of 0, 50, 100 and 200 mM. The yeast strain SU50 was inoculated in these media in a concentration of 10 cells per ml, and cultivated in a 24 well plate at 25° C. Samples were taken from a 24 well plate at regular time intervals, diluted sixty times with distilled water and measured at 660 nm to construct the growth curves. FIG. 3 shows the influence of β-gentiobiose on sub-lethal concentrations of the antifungal peptide MB21. β-Gentiobiose as such has no influence on the growth of SU-50. However, if the sub-lethal concentrations of MB21 and β-gentiobiose are combined, a clear reduction in growth potential of SU50 (10 cells per ml) was observed. At a relative high concentration of 200 mM β-gentiobiose in combination with 20 μM MB21, no growth of SU-50 was observed at all.

EXAMPLE 4

Effect of One Concentration of MB21 and a β-(1,6)-glucanase Fraction on the Growth of S. cerevisiae Strain SU 50

Figure 4:
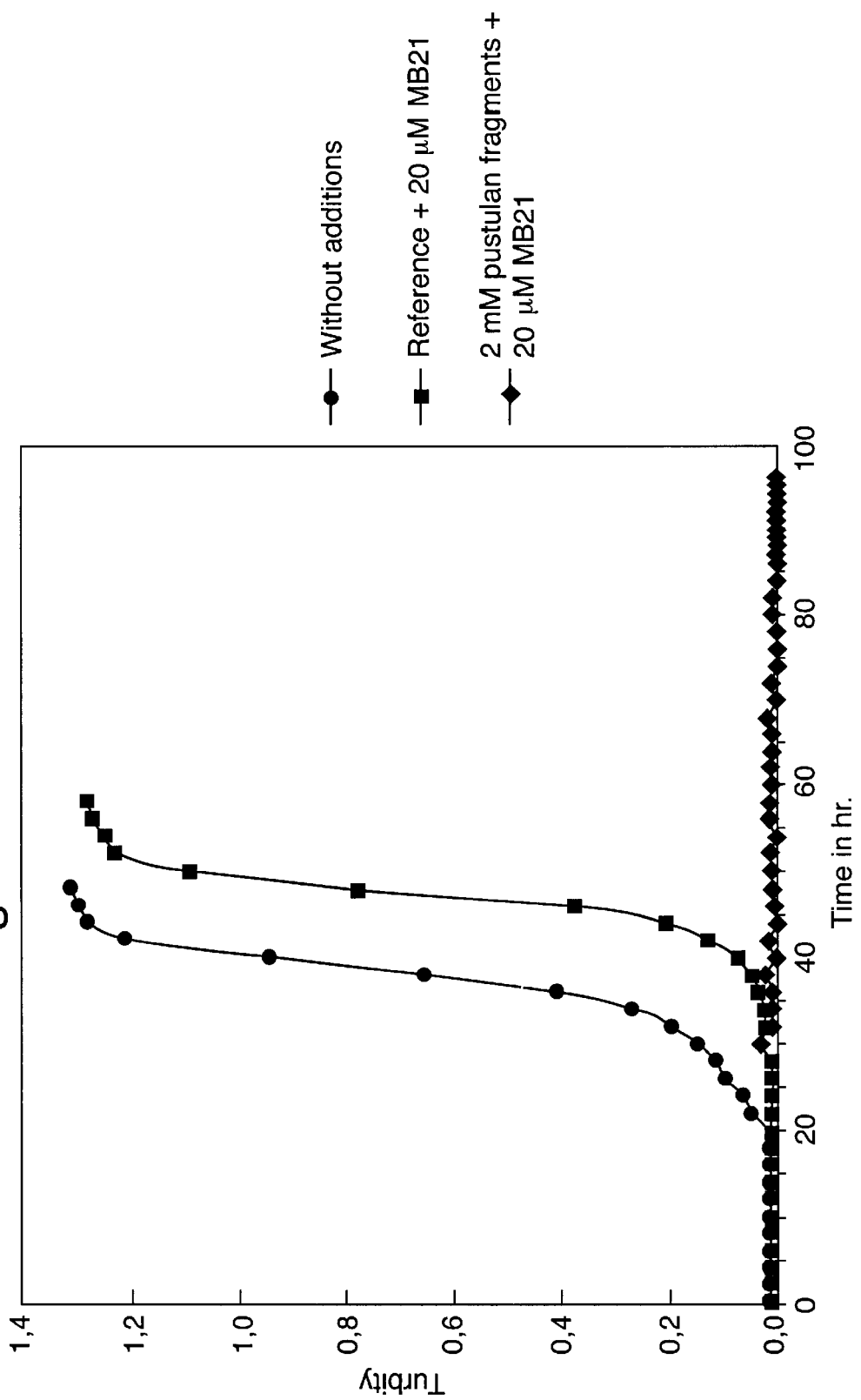
FIG. 4 shows the effect of a composition of fragmented pustulan with an average MW of 686, and MB-21 on the growth of a wild type yeast.

This example illustrates a relationship between the length of the β-(1,6)-glucan fragments and their effectiveness in competition. When the same concentration of MB21 (20 μM) was used [about 50 cells per ml] was used, a glucan fragment was obtained from pustulan with an average MW of 686, which was at least hundred times as effective as β-gentiobiose, as shown in FIG. 4.

Example 5 (Comparative)

Growth of SU 50, ZB, G1 in Presence of Various Sugars (as Comparatives) and/or MB21

In this example, three strains are grown in various media in the fashion of example 3, with the exception of being inoculated in the media in a concentration of 100 cells per ml. The sugars used are all comparatives: laminaribiose (β-1,3)-linked D-glucose), sucrose (having a 1,2 link), and sorbitol.

TABLE 1

| Example | Strain | Concentr. MB 21 (μM) | Sugar |
|---|---|---|---|
| 5-a1 | SU50 | — | — |
| 5-a2 | SU50 | 25 | — |
| 5-a3 | SU50 | 25 | 25 mM laminaribiose |
| 5-a4 | SU50 | 25 | 25 mM sucrose |
| 5-a5 | SU50 | 25 | 25 mM sorbitol |
| 5-b1 | ZB | — | — |
| 5-b2 | ZB | 6 | — |
| 5-b3 | ZB | 6 | 200 mM sucrose |
| 5-b4 | ZB | 6 | 200 mM sorbitol |
| 5-c1 | G1 | — | — |
| 5-c2 | G1 | 6 | — |
| 5-c3 | G1 | 6 | 200 mM sucrose |
| 5-c4 | G1 | 6 | 200 mM sorbitol |

Figure 5B:
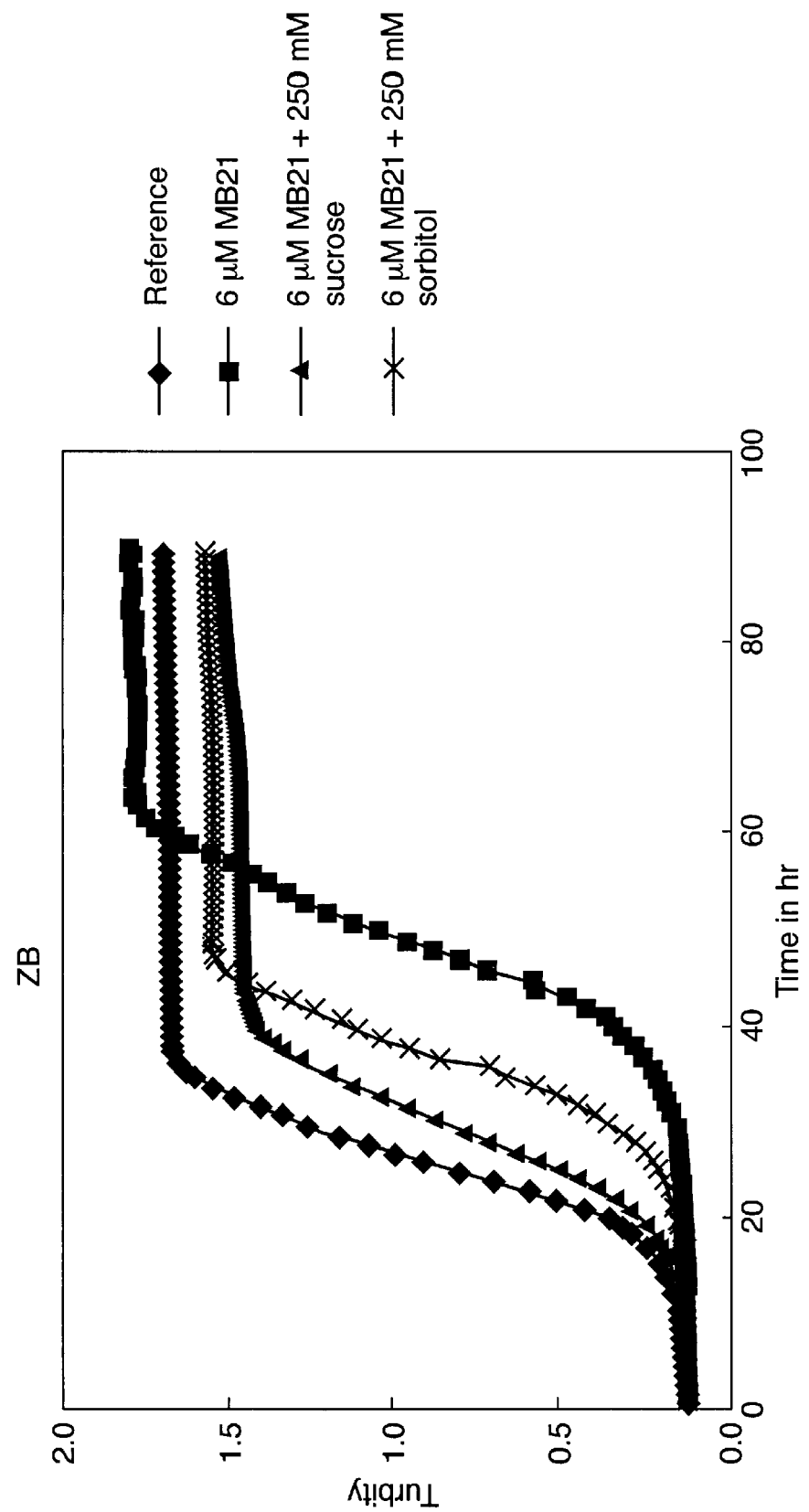
FIG. 5b shows the influence of various sugars on the growth of *Zygosaccharomyces baillii* ZB.

The results from table 1 are set out in FIGS. 5 a–c. As can be seen, if the sugars laminaribiose, sucrose, sorbitol have any effect on growth, it is a stimulating effect, as compared to the reference (no sugar, no MMAS), and when MB21 is present.

EXAMPLE 6

Growth of SU 50 in Presence of β-gentiobiose and/or MB21

In this example, strain SU 50 was grown three media (see table 2) in the fashion of example 3, with the exception of being inoculated in the media in a concentration of 100 cells per ml.

TABLE 2

| Example | Strain | Concentr. MB 21 (µM) | Sugar |
|---|---|---|---|
| 6-a | SU50 | — | 25 mM β-gentiobiose |
| 6-a | SU50 | 25 | — |
| 6-a | SU50 | 25 | 25 mM β-gentiobiose |

Figure 6:
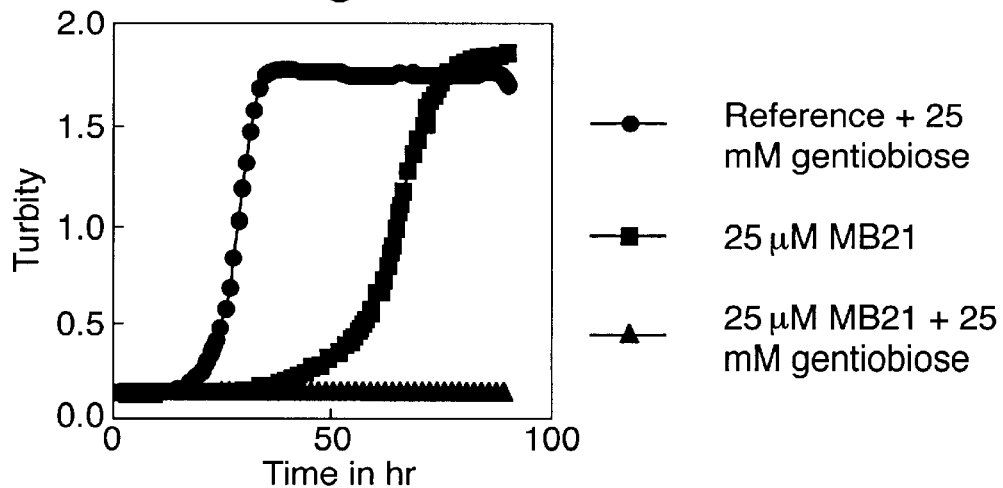
FIG. 6 shows culivation of the yeast strain *Saccharomyces cerevisiae* SU50 in the presence of β-gentiobiose, MB21, and the combination thereof.

The results are set out in FIG. 6, and are in line with example 3.

EXAMPLE 7

Growth of ZB in Presence of β-gentiobiose and/or MB21

In this example, strain ZB was grown three media (see table 3) in the fashion of example 3, with the exception of being inoculated in the media in a concentration of 100 cells per ml.

TABLE 3

| Example | Strain | Concentr. MB 21 (µM) | Sugar |
|---|---|---|---|
| 7-a | ZB | — | 200 mM β-gentiobiose |
| 7-a | ZB | 6 | — |
| 7-a | ZB | 6 | 200 mM β-gentiobiose |

Figure 7:
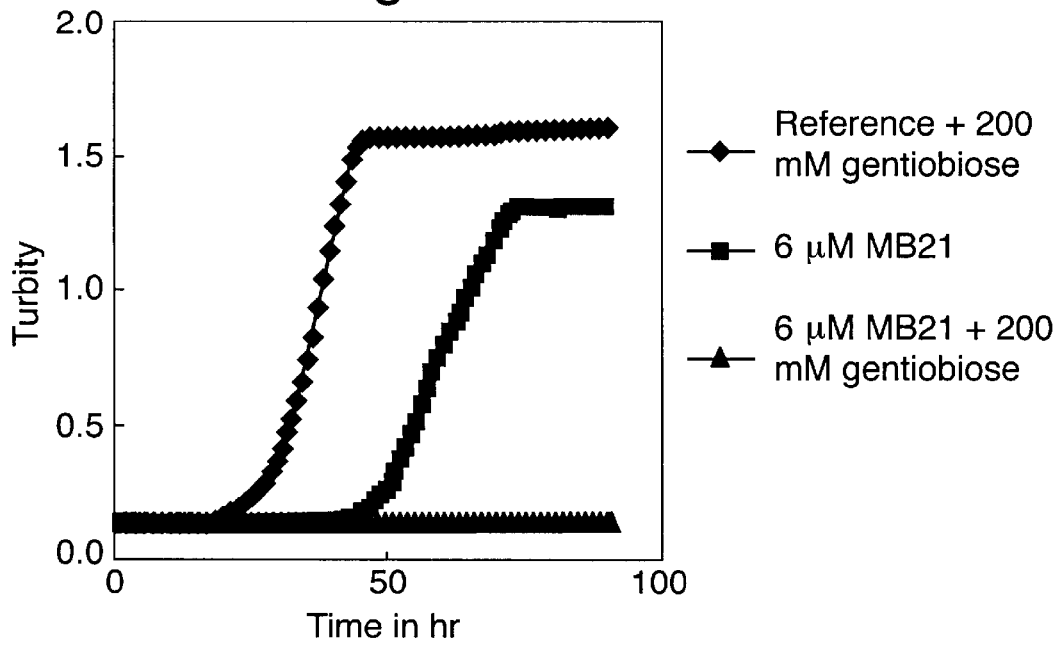
FIG. 7 shows culivation of the yeast strain *Zygosaccharomyces bailii* ZB in the presence of β-gentiobiose, MB21, and the combination thereof.

The results are set out in FIG. 7, and are for the different strain similar to the results for SU50 as in examples 3 and 6.

EXAMPLE 8

Growth of G1 in Presence of β-gentiobiose and/or MB21

In this example, strain G1 was grown three media (see table 4) in the fashion of example 3, with the exception of being inoculated in the media in a concentration of 100 cells per ml.

TABLE 4

| Example | Strain | Concentr. MB 21 (µM) | Sugar |
|---|---|---|---|
| 8-a | G1 | — | 200 mM β-gentiobiose |
| 8-a | G1 | 6 | — |
| 8-a | G1 | 6 | 200 mM β-gentiobiose |

Figure 8:
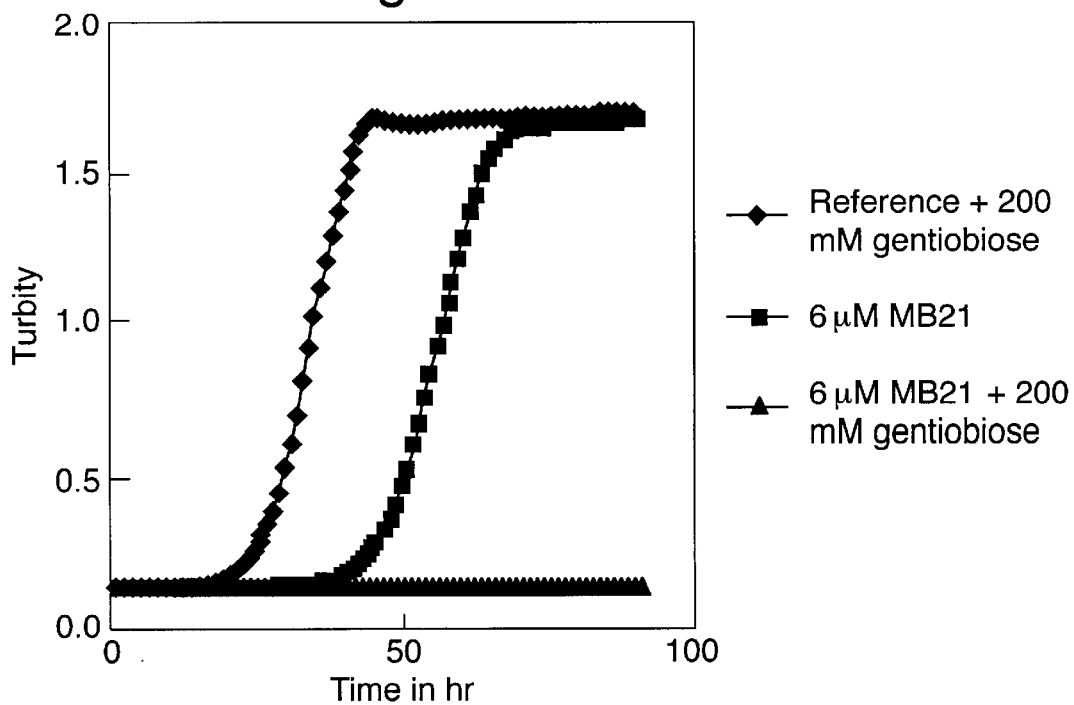
FIG. 8 shows culivation of the yeast strain *Zygosaccharomyces bailii* G1 in the presence of β-gentiobiose, MB21, and the combination thereof.

The results are set out in FIG. 8, and are for the different strain similar to the results for SU50 as in examples 3 and 6.

EXAMPLE 9

Inhibition of *Zygosaccharomyces bailli* G1 in Presence of a β-(1,6)-glucan of Chain Length 2–5 and MB21

Figure 9:
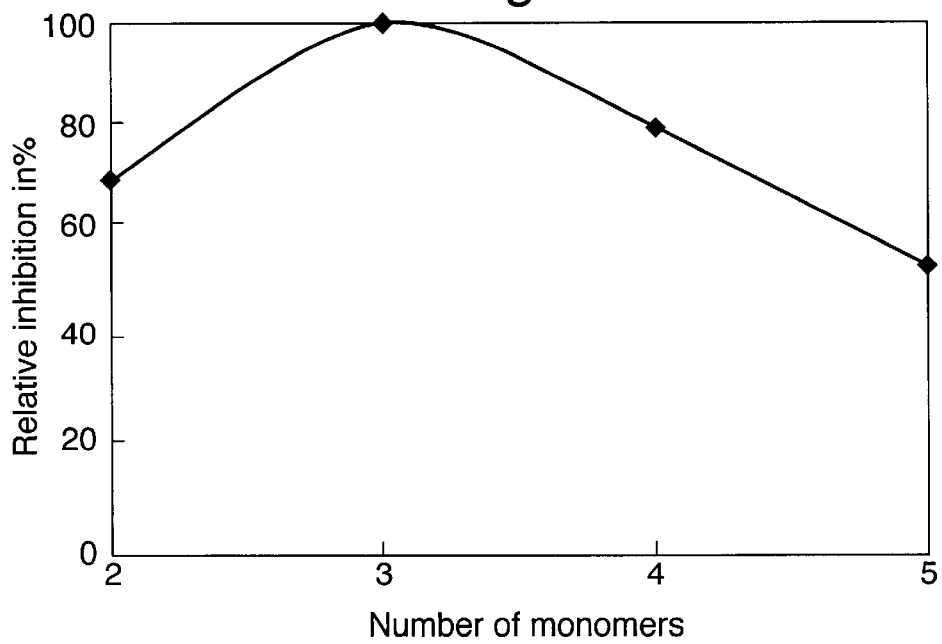
FIG. 9 shows the inhibition (relative) of *Zygosaccharomyces bailii* G1 in the presence of MB21 in combination with β-(1,6)-glucose polysaccharides having an average number of monomers of 2, 3, 4 and 5.

In this example, strain G1 was grown in the fashion of example 3 (with the exception of being inoculated in the media in a concentration of 100 cells per ml) in the presence of 6 µM MB21 and 50 mM of a β-(1,6)-glucan. Experiments were done with short-chain β-(1,6)-glucan of variable chain length. Chain length 2 is β-(-gentiobiose, and as such relatively pure. The β-(1,6)-glucans with number of monomers of 3, 4 and 5 (all average) were obtained by breaking down pustulan and subsequent fractionation. The result (relative inhibition) is set out in FIG. 9. As can be seen, all β-(1,6)-glucose polysaccharides having 2–5 monomers (in the backbone) do enhance the inhibition of growth by MB21.

REFERENCES

1. Roman Kollár, Bruce B. Reinhold, Eva Petráková, Herman J. C. Yeh, Gilbert Ashwell, Jana Drgonová, Johan C. Kapteyn, Frans M. Klis, and Enrico Cabib, (1997). Architecture of the yeast cell wall. *The Journal of Biochemical Chemistry* 272:17762–17775.

2. Dea-Jin Yun, Yuan Zhao, José M. Pardo, Meena L. Narasimhan, Barbara Damsz. Hyeseung Lee, Laura R. Abad, Matilde Paino D'Urzo, Paul M. Hasegawe, and Ray A. Bressan, (1997). Stress proteins on the yeast cell surface determine resistance to osmotin, a plant antifungal protein. *Proc. Natl. Acad. Sci. USA* 94:7082–7087 Plant Biology.

3. Brul S., King A., Van der Vaart J. M., Chapman J. W., Klis F. M., and Verrips C. T., (1997), The incorporation of mannoproteins in the cell wall of Saccharomyces cerevisiae and filamentous Ascomycetes. Antonie van Leeuwenhoek 72:229–237.

4. Orlean P. (1997). Biogenesis of yeat wall and surface components. In: The Molecular and Cellular Biology of the yeast Saccharomyces; Cell cycle and Cell Biology (Prongle J. R., Broach J. R., Jones E. W., eds) pp. 229–362, Cold Spring Harbor Laboratory Press, Cold Spring Harbor, N.Y.

5. Van Berkel, M. (1998). Glycosylation and anchoring of proteins in the cell wall of *Saccharomyces cerevisiae*, PhD thesis, University of Amsterdam, the Netherlands.

6. Roemer T., Paravicini G., Payton M. A., and Bussey H. (1994). Characterisation of the yeast 1-6-β-glucan biosynthetic components, Kre1p and Shn1p, and genetic interactions between the PKC1 pathway and extracellular matrix assembly, *J. Cell. Biol.* 127:567–579.

7. Vaart van der J. M., Schagen van F. S., Mooren A. T., Chapman J. W., Klis F. M., and Verrips C. T. (1996). The retention mechanism of cell wall proteins in *Saccaromyces cerevisiae*. Wall-bound Cwpep is β-1,6 -glycosylated. *Biochimica et Biophysica Acta* 1291:206–214.

8. Bradford M., (1976). A rapid and sensible method for the quantification of microgram quantities of protein utilizing the principle of protein-dye binding. *Anal. Biochem.* 72:248.

9. Jesús de la Cruz, José A., Pintor-Toro, Tahía Benítez, and Antonio LLobell., Purification and characterization of an Endo-β-(1,6)-Glucanase from *Trichoderma harzianum* that is related to its *Mycoparasitism. Journal of Bacteriology.* 1995, 177:1864–1871.

10. Bom I. J., Dielbandhoesing S. K., Harvey K. N., Oomes S. J. C. M., Klis F. M., Brul S. (1998). A new tool for studying the molecular architecture of the fungal cell wall: one-step purification of recombinant Trichiderma β-(1,6)-glucanase expressed in *Pichia pastoris. Biochimica et Biophysica Acta* 1425:419–424.

11. Dielbandhoesing S. K., Zhang H., Caro L. H. P., Van der Vaart J. M., Klis F. M., Verrips C. T. and Brul S. (1998). Specific Cell Wall Proteins Confer Resistance to Nisin upom Yeast Cells. *Applied and Environmental Microbiology* 64:4047–4052.

What is claimed is:

1. A composition suitable for inhibiting the outgrowth of fungi wherein said composition comprises:

a first ingredient which inhibits the biogenesis of a normal fungal cell wall, said first ingredient being selected from the group consisting of β-gentiobiose, fragmented pustulan and mixtures thereof, and a second ingredient which perturbs the structure of the cellular membrane of said fungi, so that either the cellular integrity is essentially lost or cell division cannot take place, or both, said second ingredient being selected from the group consisting of MB-21, nisin, carvacrol, sorbic acid and mixtures thereof.

2. The composition of claim 1, wherein the first ingredient is present at a concentration of 0.05 to 20% by total weight of the composition.

3. The composition of claim 1, wherein the second ingredient is present at a concentration of $5\times10^{-5}$ to $1\times10^{-2}$% by total weight of the composition.

4. The composition of claim 1, which is added to a food product or to a personal care product.

5. Composition according to claim 4, wherein the food product is selected from the group consisting of sauces, sauce-bases, dressings, ketchups, soups, soup-bases, spreads, beverages, and ice cream.

6. Composition according to claim 4, wherein the personal care product is selected from the group consisting of skin creams, lotions, ointments, shampoos and other products for application to hair.

7. The composition of claim 1, wherein the first ingredient is present at a concentration of 0.1 to 1% by total weight of the composition.

8. The composition of claim 1, wherein the second ingredient is present at a concentration of $1\times10^{-4}$ to $2.5\times10^{-3}$% by total weight of the composition.

* * * * *

SEQUENCE LISTING

```
<160> NUMBER OF SEQ ID NOS: 1

<210> SEQ ID NO 1
<211> LENGTH: 15
<212> TYPE: PRT
<213> ORGANISM: Unknown
<220> FEATURE:
<223> OTHER INFORMATION: fungal cell wall lytic enzyme

<400> SEQUENCE: 1

Phe Ala Ser Leu Leu Gly Lys Ala Leu Lys Ala Leu Ala Phe Gln
1               5                   10                  15
```